United States Patent

Drobnitzky et al.

[11] Patent Number: 5,879,298
[45] Date of Patent: Mar. 9, 1999

[54] CONTROL UNIT FOR A MEDICAL DEVICE

[75] Inventors: Matthias Drobnitzky, Aachen; Gerald Lenz, Neunkirchen am Brand; Henrik Krogmann, Erlangen; Rainer Kuth, Herzogenaurach, all of Germany

[73] Assignee: Siemens Aktiengesellschaft, Munich, Germany

[21] Appl. No.: 874,150

[22] Filed: Jun. 13, 1997

[30] Foreign Application Priority Data

Jun. 19, 1996 [DE] Germany .................. 196 24 517.6

[51] Int. Cl.⁶ .................................................. A61B 5/05
[52] U.S. Cl. .................. 600/407; 600/126; 297/217.1
[58] Field of Search ................................ 600/126, 407; 297/217.1, 217.2, 217.3, 463.2

[56] References Cited

U.S. PATENT DOCUMENTS

| | | |
|---|---|---|
| 4,854,301 | 8/1989 | Nakajima ........................... 600/102 |
| 5,098,426 | 3/1992 | Sklar et al. ......................... 606/5 |
| 5,259,365 | 11/1993 | Nishikori et al. ................... 600/102 |
| 5,271,379 | 12/1993 | Phan et al. ........................ 600/104 |
| 5,339,799 | 8/1994 | Kami et al. ....................... 600/117 |
| 5,365,927 | 11/1994 | Roemer et al. .................... 600/410 |
| 5,524,180 | 6/1996 | Wang et al. ....................... 600/118 |
| 5,605,531 | 2/1997 | Lane et al. ....................... 600/118 |

FOREIGN PATENT DOCUMENTS

OS 41 25 313  2/1993  Germany .

*Primary Examiner*—Brian L. Casler
*Attorney, Agent, or Firm*—Hill & Simpson

[57] ABSTRACT

A control unit for a medical device has an actuation part and an electrical signal output that, due to an actuation of the actuation part, emits a control signal for a control computer of the medical device. The actuation device is secured to a work chair at the level of the heel of the foot of a person on the work chair.

5 Claims, 2 Drawing Sheets

CONTROL UNIT FOR A MEDICAL DEVICE

BACKGROUND OF THE INVENTION

1. Field of the Invention

The present invention is directed to a medical device control unit of the type having an actuation part and an electrical signal output that, due to an actuation of the actuation part, emits an electrical control signal for a control computer of the medical device.

2. Description of the Prior Art

A control unit of the above general type is known from German OS 4 125 313. A foot switch from which control signals are transmitted to a central control unit is thereby provided for controlling a dental treatment apparatus. The foot switch is actuated with the sole of the foot, for example the heel or ball region.

A control unit of the type initially described is also disclosed in U.S. Pat. No. 5,365,927. This control unit has a foot switch fashioned as an actuation part for use in conjunction with a magnetic resonance apparatus. The foot switch is arranged immediately next to the magnetic resonance apparatus and can be actuated by a physician or an examining person during medical procedures being performed on a patient supported in the magnetic resonance apparatus. The foot switch is connected via evaluation electronics to a control computer of the magnetic resonance apparatus, and its actuation causes magnetic resonance image datasets, corresponding to those image regions that the physician or examining person previously marked with a hand-held pointer, to be displayed on a monitor. It is advantageous in this context that the physician or examining person can operate the magnetic resonance system via the foot switch without having to use his other hands, which are in the sterile work field. It could be disadvantageous in some situations, however, if the physician or examining person would have to turn his or her eyes away from the patient in order to seek the foot switch before its actuation. When the physician or examining person is seated during the examination, care would have to be exercised to be sure that the foot switch is placed in a proximity within reach of the foot.

SUMMARY OF THE INVENTION

An object of the present invention is to provide a control unit for medical apparatus that can be easily and reliably operated by a seated physician or examining person.

The above object is achieved in accordance with the principles of the present invention in a medical apparatus control unit having an actuation component, actuatable by a physician or an examination attendant at the medical device, which upon actuation emits an electrical signal to a control computer which operates the medical device, the actuation component being secured to a work chair at a height coinciding with the location of the heel of a person seated on the work chair, so that the actuation component can be actuated by a side region of the foot of physician or examination attendant.

In an embodiment the actuation part is a closed pressure bellows, and in that the pressure bellows is connected via a hose conduit to a pressure transducer i.e., a transducer which emits an electrical signal when acted on by a suitable degree of pressure. The pressure transmission is in turn connected to evaluation electronics, the evaluation electronics emits an electrical control signal upon a suitable magnitude of pressure acting on the transducer. The control unit is thus compatible with the cleaning and sterilization requirements of clinical operating rooms. In particular, the control unit, even without further measures, meets the demands made of the electromagnetic compatibility of diagnostic magnetic resonance systems because all electrical components of the pressure-electrical transducer can be arranged outside the radio-frequency space.

In another embodiment the evaluation electronics generates the control signal due to a change in the pressure occurring at the pressure-electrical transducer. A hose conduit having a smaller inside diameter can then be used, compared to that needed for a static pressure transducer. If the hose conduit is stepped on or when something rolls over it, because of its small inside diameter only a small pressure wave is generated that is recognized by the evaluation electronics as a noise signal and can be blanked out.

In another embodiment for use in conjunction with a computer keyboard, the electrical control signal from the evaluation electronics corresponds to a control signal triggered by a function key of the computer keyboard. The control unit can thus be connected into conventional systems without requiring hardware or software modifications. The installation of the control unit is thus very simple and could even be retrofitted in existing systems already in use.

In a further embodiment the electrical control signal corresponds to a digital word that can be emitted by a function key of the computer keyboard. The function triggered by the control unit can thus be programmed like the function keys of a standard keyboard.

DESCRIPTION OF THE PREFERRED EMBODIMENTS

Figure 1:
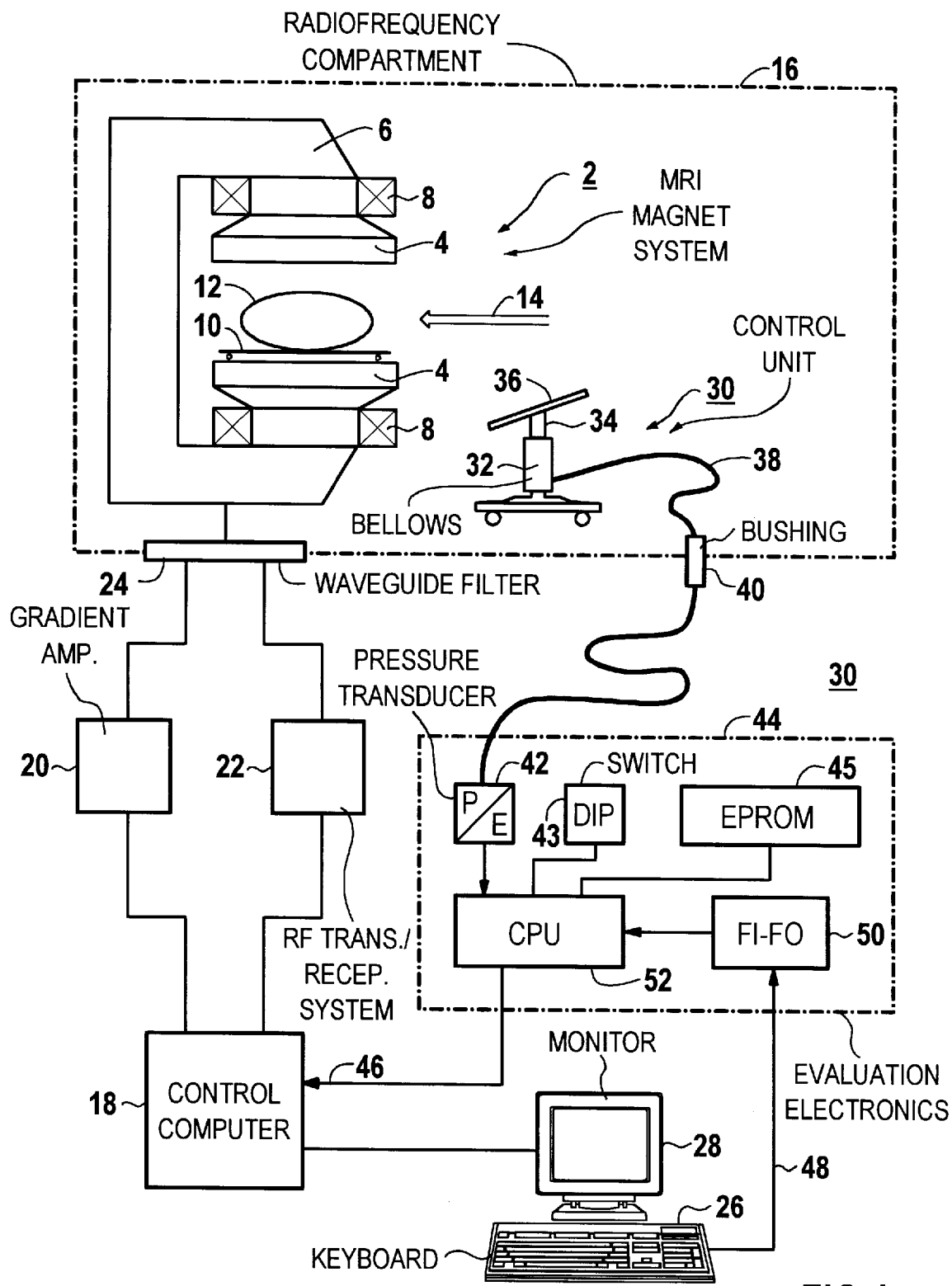
FIG. 1 is an overview of a diagnostic magnetic resonance apparatus with an inventive control unit.

As a medical apparatus to be controlled, FIG. 1 shows the schematic structure of a diagnostic magnetic resonance apparatus. The actual examination part of the magnetic resonance apparatus is composed of an open magnet system 2 with two pole shoes 4 arranged opposite one another that are connected to one another via a C-shaped magnetic return 6. The magnetic drive is composed of respective electromagnet windings 8 arranged at the pole shoes 4. In an approximately spherical region, the magnet system 2 generates a uniform and vertically aligned basic magnetic field between the pole shoes 4. A region of a patient 12 to be examined is positioned within the uniform basic magnetic field region on a patient support 10. In addition to the patient access, a lateral access symbolized by an arrow 14 is established for a physician or examining person. Gradient coils for generating gradient fields in three directions residing perpendicularly on one another as well as radio-frequency antennas for exciting or receiving magnetic resonance signals are present in a known manner, but are not shown. The magnet system 2, including the gradient coils and radio-frequency antennas, is located in a radio-frequency compartment 16. A control computer 18, which generates the control signals required for the operation, is arranged outside the radio-frequency compartment 16. These control signals are the control signals for gradient amplifiers 20, likewise arranged outside the radio-frequency compartment, and for a radio-frequency transmission/ reception system 22. The high-power output signals of the gradient amplifiers 20 and of the radio-frequency transmission/reception system 22 are conducted into the radio-frequency compartment 16 via waveguide filters 24. A keyboard 26 is arranged outside the radio-frequency compartment 16. A monitor 28 is likewise connected to the control computer 18.

In addition, a control unit 30, via which a physician located inside the radio-frequency compartment 16, for example during a magnetic resonance-guided procedure, can operate the magnetic resonance system, is connected to the control computer 18. The control unit 30 is ergonomically fashioned for a seated position, so that it can be actuated with a foot or a heel without a change in the operator's position. The control unit 30 includes a pressure bellows 32 forming an actuation part that is secured to a post 34 of a work chair 36. A hose conduit 38 has one end connected to the lower part of the pressure bellows 32 and is conducted out of the radio-frequency compartment 16 via a radio-frequency-tight bushing 40. The bushing 40 is composed essentially of an elongated, conductive hollow cylinder. The other end of the hose conduit 38 is connected to a pressure-electrical transducer 42 that converts a pressure signal transmitted via the hose conduit into an electrical signal.

The pressure transducer 42 can be a dynamic pressure transducer, such as with a spring-supported coil arranged so as to be movable in a magnetic field. A movement of the coil in the magnetic field due to a pressure wave emanating from the pressure bellows 32 induces a voltage pulse that is processed by evaluation electronics 44 to form an output signal of the control unit 30. The control unit 30 emits the output signal at an output 46. The output signal corresponds to a digital word such as can be emitted by depression of a function key of the computer keyboard 26. The digital word can be programmed and prescribed via miniature switches 43 and/or a memory 45. The digital word can likewise be programmable via a flash memory card that is not shown in FIG. 1.

The output 46 produced in a signal path that includes an electrical connecting line 48 that connects the computer keyboard 26 to the evaluation electronics 44, and leads to the control computer 18. A data word emitted by the computer keyboard 26 is intermediately stored in a buffer memory 50 that is organized according to the "first in first out" principle (FIFO). A processor 52 in the evaluation electronics 44 receives an interrupt signal if the pressure bellows 32 was actuated, and transmits the data word from the keyboard 26 to the control computer 18 only if the pressure bellows 32 was not actuated. The magnetic resonance apparatus can be operated and the function linked to the signal or word can thus be started by an operator upon actuation of the corresponding function key, but also by a physician or examining person in the radio-frequency compartment 16 by actuating the pressure bellows 32.

Figure 2:
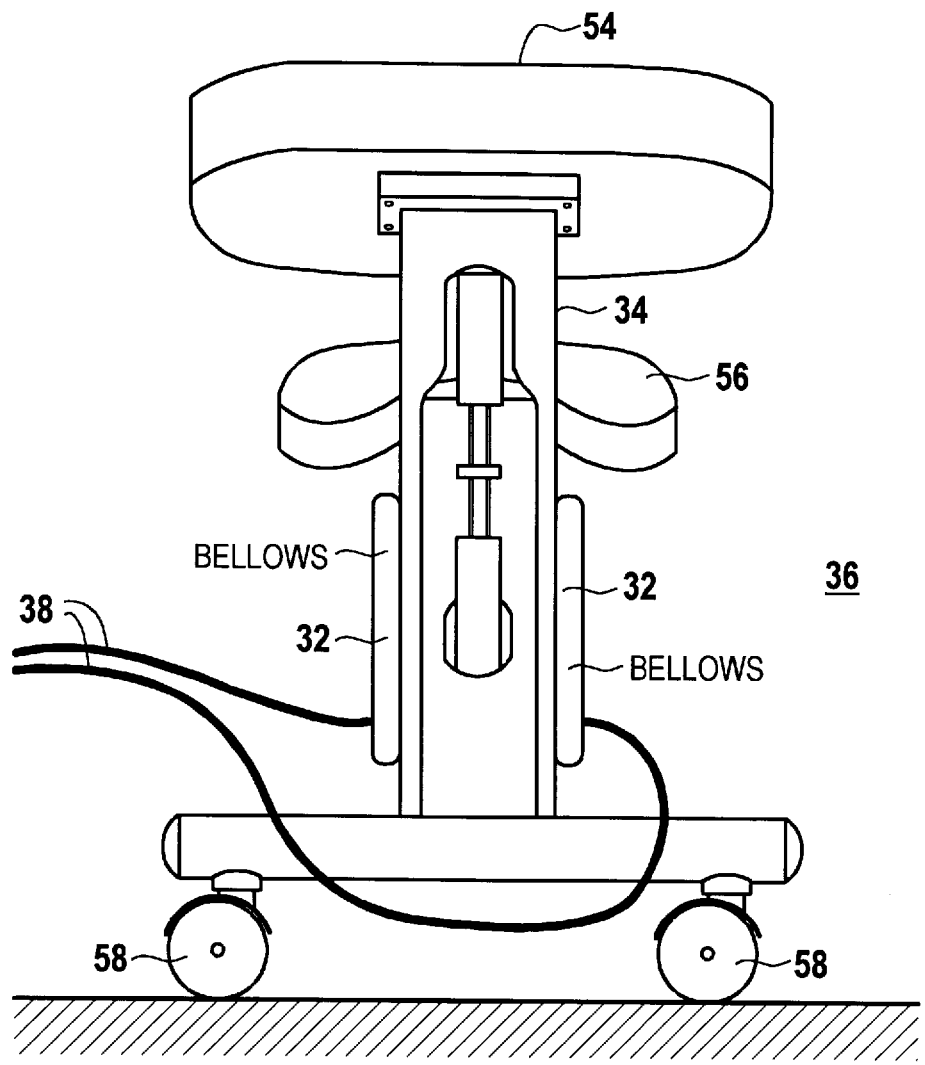
FIG. 2 shows a front view of a kneeler stool with laterally secured pressure bellows fashioned as actuation parts in accordance with the invention.

In a front view, FIG. 2 shows a kneeler stool fashioned as work chair having a seat 54 and a knee support 56 that are both carried by the central column 34. The work chair 36 is provided with rollers 58 for movement. Two elongated, pneumatic pressure bellows 32 are secured opposite one another at both sides of the column 34 at the level of the heel of the foot. By pivoting the right or left heel, the physician can exert pressure on the corresponding pressure bellows 32. The arising pressure wave is then supplied to the evaluation electronics via the hose conduit 38 connected to the pressure bellows 32. Due to the change in pressure exerted by the pressure wave at the pressure transducer 42, the correspondingly programmed data word is emitted as an output signal at the output 46.

Although modifications and changes may be suggested by those skilled in the art, it is the intention of the inventors to embody within the patent warranted hereon all changes and modifications as reasonably and properly come within the scope of their contribution to the art.

We claim as our invention:

1. In a medical device operated by a control computer having a computer keyboard, the improvement of a control unit for said medical device comprising:

a work chair adapted to receive a medical device operator;

an actuation element disposed on said work chair at foot level, and adapted to be actuated with a side of a foot of a medical device operator on said work chair;

means, upon actuation of said actuation element, for emitting an electrical control signal to said control computer for controlling said medical device, and said actuation element comprising a closed pressure bellows connected to a hose conduit, and wherein said means for emitting said control signal comprising a pressure transducer in communication with said hose conduit which emits an electrical signal upon compression of said bellows, and electronic evaluation means, supplied with said electrical signal, for generating said control signal upon compression of said bellows.

2. A control unit as claimed in claim 1 wherein said work chair has a vertical supporting column, and wherein said pressure bellows is elongated and has a longitudinal direction, and wherein said bellows is attached to said supporting column with said longitudinal direction substantially vertically oriented.

3. The improvement of claim 1 wherein said electronic evaluation means comprises means for generating said control signal dependent on a pressure change at said pressure transducer.

4. The improvement of claim 1 wherein said means for emitting said control signal upon actuation of said actuation element comprises means for emitting a control signal substantially identical to a function control signal emitted by said computer keyboard.

5. The improvement of claim 4 wherein said function control signal and said control signal each comprise a data word.

* * * * *